(12) United States Patent
Nakajima et al.

(10) Patent No.: US 7,537,703 B2
(45) Date of Patent: *May 26, 2009

(54) HIGH-ENDURANCE PACKING MATERIAL FOR LIQUID CHROMATOGRAPHY

(75) Inventors: Osakazu Nakajima, Osaka (JP); Takeshi Urano, Narita (JP)

(73) Assignee: Daiso Co., Ltd., Osaka-shi (JP)

( * ) Notice: Subject to any disclaimer, the term of this patent is extended or adjusted under 35 U.S.C. 154(b) by 419 days.

This patent is subject to a terminal disclaimer.

(21) Appl. No.: 10/574,419

(22) PCT Filed: Jun. 22, 2005

(86) PCT No.: PCT/JP2005/011437

§ 371 (c)(1),
(2), (4) Date: Apr. 4, 2006

(87) PCT Pub. No.: WO2006/001300

PCT Pub. Date: Jan. 5, 2006

(65) Prior Publication Data

US 2008/0249326 A1    Oct. 9, 2008

(30) Foreign Application Priority Data

Jun. 23, 2004   (JP)   .............................. 2004-184678

(51) Int. Cl.
*B01D 15/08*   (2006.01)

(52) U.S. Cl. ..................... 210/656; 210/635; 210/198.2; 210/502.1

(58) Field of Classification Search ................. 210/635, 210/656, 659, 198.2, 502.1; 502/401, 439
See application file for complete search history.

(56) References Cited

U.S. PATENT DOCUMENTS 5,134,110 A * 7/1992 Sudo et al. .................. 502/401

(Continued)

FOREIGN PATENT DOCUMENTS

JP    63-137750    6/1988

(Continued)

OTHER PUBLICATIONS

Aue, Walter A. et al., "Bonded Phases" From Cyclic Organosilicons for Gas and Liquid Chromatography, Journal of Chromatography, vol. 200, pp. 3-13, 1980.

*Primary Examiner*—Ernest G Therkorn
(74) *Attorney, Agent, or Firm*—Oblon, Spivak, McClelland, Maier & Neustadt, P.C.

(57) ABSTRACT

The present invention provides a highly durable packing material for liquid chromatography that is excellent in acidic resistance and alkalic resistance. Such a packing material for liquid chromatography can be obtained by chemically modifying silica gel with a bifunctional silane compound represented by the general formula [I], and carrying out an endcapping reaction of the resulting chemically modified silica gel using bifunctional cyclic silazane represented by the general formula [II]. In the formula [I], $X^1$ and $X^2$, the same or different, represent a hydrogen atom, a halogen atom or an alkoxy group having 1 to 4 carbon atoms; and $R^1$ represents an alkyl group or an aryl group, which can have substituent(s). In the formula [II], $R^2$ and $R^3$, the same or different, represent an alkyl group having 1 to 4 carbon atoms; and n represents a value indicating unit number that forms the ring, which is an integer of 2 to 10.

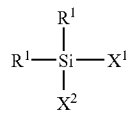

[I]

3 Claims, 1 Drawing Sheet

U.S. PATENT DOCUMENTS

| | | | |
|---|---|---|---|
| 7,033,505 B2 * | 4/2006 | Urano | 210/656 |
| 2004/0159611 A1 * | 8/2004 | Urano | 210/656 |
| 2006/0175238 A1 * | 8/2006 | Lautamo | 210/198.2 |
| 2006/0219636 A1 * | 10/2006 | Plumb et al. | 210/656 |
| 2008/0249326 A1 * | 10/2008 | Nakajima et al. | 556/410 |

FOREIGN PATENT DOCUMENTS

| | | |
|---|---|---|
| JP | 04-212058 | 8/1992 |
| JP | 10-206407 | 8/1998 |
| JP | 2003-149219 | 5/2003 |
| JP | 2004-271522 | 9/2004 |

* cited by examiner

HIGH-ENDURANCE PACKING MATERIAL FOR LIQUID CHROMATOGRAPHY

REFERENCE TO RELATED APPLICATION

This application is a 371 PCT/JP05/11437 filed Jun. 22, 2005.

TECHNICAL FIELD

The present invention relates to a method of the production of a packing material for liquid chromatography.

Liquid chromatography has been used in a wide range of fields as important means for separation analyses in fields of medical drugs, foods, natural compounds and the like. In general, as a packing material for liquid chromatography, porous silica gel having excellent mechanical strength, favorable separation performance and the like which had been chemically modified on the surface thereof with a silane compound has been used in many cases. Most common surface-modified silica gel has octadecyl groups introduced to the silanol group on the surface via a chemical bond (ODS), however, those having octyl groups, butyl groups, methyl groups or the like as the introduced group have been also known. In some cases, those alkyl groups have a functional group such as a phenyl group, an amino group, a cyano group or a nitro group at the end thereof.

In analysis and fractionation of a compound by liquid chromatography, an acidic mobile phase or an alkalic mobile phase is often used as the separation condition. Particularly, when a biological sample containing peptides, proteins or the like is analyzed and fractionated, problems of detachment of modifying group from the matrix silica gel through hydrolysis with acid, dissolution of the matrix silica gel by alkali, and the like may be raised. Accordingly, a highly durable packing material for liquid chromatography having longer operating life has been demanded.

TECHNICAL BACKGROUND

Conventionally, as methods of the production of a highly durable packing material for liquid chromatography, a method which comprises impregnating a silica gel surface with polysilazane such as perhydroxypolysilazane, then baking this silica gel to form ceramic coatings on its surface to coating with ceramics, and chemically bonding a silane compound as a modification agent thereto (see, Patent Document 1), a method which comprises polymerizing a silicone compound having a hydrosilyl group on a silica gel surface to form a silicone polymer (see, Patent Document 2), and a method in which monofunctional silane having a steric protection group such as octadecyldi-t-butylchlorosilane or octyldiisopropyl chlorosilane in its structure is used as a silane compound to be a modification agent (Patent Document 3) were proposed.

However, any of the coating with ceramics in Patent Document 1, and the coating with a polymer in Patent Document 2 may possibly deteriorate the characteristics of the silica gel, while the steric protection group in Patent Document 3 may greatly change the selectivity of as a packing material for liquid chromatography.

Patent Document 1: JP-A-H10-206407.
Patent Document 2: JP-A-2003-149219.
Patent Document 3: JP-A-S63-137750.

DISCLOSURE OF THE INVENTION

Problems that the Invention is to Solve

In view of the foregoing situation, an object of the present invention is to provide a highly durable packing material for liquid chromatography that is excellent in acidic resistance and alkalic resistance.

Means for Solving the Problems

The present inventor elaborately investigated in order to solve the problems as described above, and consequently accomplished a method of the production of a novel highly durable packing material for liquid chromatography that is extremely excellent in acidic resistance and alkalic resistance, the method comprising a step of chemically modifying the silica gel surface using a silane compound having a particular structure, and the following endcapping reaction step in which a bifunctional cyclic silazane compound having a particular structure is used, without loss of characteristics of the silica gel, and without change of selectivity of a packing material for liquid chromatography.

Accordingly, the present invention is a method of the production of a packing material for liquid chromatography which comprises chemically modifying silica gel with a bifunctional silane compound represented by the general formula [I]:

$$R^1-\underset{\underset{X^2}{|}}{\overset{\overset{R^1}{|}}{Si}}-X^1 \quad [I]$$

[wherein, $X^1$ and $X^2$, the same or different, represent a hydrogen atom, a halogen atom or an alkoxy group having 1 to 4 carbon atoms; and $R^1$ represents an alkyl group or an aryl group which can have substituent(s)], and carrying out an endcapping reaction of the resulting chemically modified silica gel using bifunctional cyclic silazane represented by the general formula [II]:

$$\left(\underset{\underset{R^3}{|}}{\overset{\overset{R^2}{|}}{Si}}-\overset{H}{\underset{|}{N}}\right)_n \quad [II]$$

[wherein, $R^2$ and $R^3$, the same or different, represent an alkyl group having 1 to 4 carbon atoms; and n represents a value indicating unit number that forms the ring, which is an integer of 2 to 10].

Furthermore, the invention provides a column for liquid chromatography in which the packing material for liquid chromatography obtained by the aforementioned method is used, and a method of the analysis or a method of the fractionation in which the column is used, in particular, a method of the analysis or fractionation of peptides or proteins included in a biological sample.

Raw material silica gel which may be preferably used in the method of the invention is porous silica gel having a mean particle size of usually 1 to 1000 μm, and preferably 2 to 200 μm; having a fine pore size of usually 10 to 10000 angstrom, and preferably 50 to 3000 angstrom; and having a surface area of usually 1 to 1000 m²/g, and preferably 5 to 600 m²/g. For achieving high separation performance, one having high purity and spherical shape is preferred as the raw material silica gel.

In the bifunctional silane compound represented by the general formula [I], the alkyl group represented by $R^1$ can be a straight alkyl group, a branched alkyl group, a cyclic alkyl group or the like. When $R^1$ represents an alkyl group, number of the carbon atom is not particularly limited, but can be preferably 1 to 30, and more preferably 2 to 8. The aryl group represented by $R^1$ can be a phenyl group, a tolyl group, a mesityl group, a naphthyl group or the like.

The alkyl group represented by $R^1$ in the general formula [I] can have an aryl group, an amino group (—NH), a cyano group (—CN) or a nitro group (—NO) at the end thereof, or can have an amide group (—NH—C(O)—), a carbamate group (—O—C(O)—NH—), a carbamide group (—NH—C(O)—NH—), an ester group (—O—C(O)—) or a carbonate group (—O—C(O)—O—) at a site other than the end thereof.

The bifunctional silane compound represented by the general formula [I] is dialkylsilane or diaryl silane having a hydrogen atom, a halogen atom or an alkoxyl group. Specific examples include dimethyldichlorosilane, dimethyldimethoxysilane, dimethyldiethoxysilane, diethyldichlorosilane, diethyldimethoxysilane, diethyldiethoxysilane, di-n-propyldichlorosilane, di-n-propyldimethoxysilane, diisopropyldichlorosilane, diisopropyldimethoxysilane, di-n-butyldichlorosilane, di-n-butyldimethoxysilane, diisobutyldichlorosilane, diisobutyldimethoxysilane, di-t-butyldichlorosilane, di-t-butyldimethoxysilane, di-n-pentyldichlorosilane, di-n-pentyldimethoxysilane, dicyclopentyldichlorosilane, dicyclopentyldimethoxysilane, di-n-hexyldichlorosilane, di-n-hexyldimethoxysilane, dicyclohexyldichlorosilane, dicyclohexyldimethoxysilane, di-n-heptyldichlorosilane, di-n-heptyldimethoxysilane, di-n-octyldichlorosilane, di-n-octyldimethoxysilane, diphenyldichlorosilane, diphenyldimethoxysilane, dimesityldichlorosilane, dimesityldimethoxysilane, di-(p-tolyl)-dichlorosilane, bis(3-cyano propyl)dichlorosilane, bis(3-cyanopropyl) dimethoxysilane and the like.

The present inventors performed a variety of studies, and consequently found that the silica gel chemically modified using a bifunctional silane compound represented by the general formula [I] as a chemical modification agent is markedly effective in improving durability, in comparison with the silica gel chemically modified using a conventional monofunctional silane compound.

The chemical modification reaction can be carried out by a known method and under known conditions, in which the silica gel and the bifunctional silane compound [I] can be heated in a solvent to permit the reaction. The reaction temperature is preferably 60 to 200° C., and more preferably 100 to 160° C. The reaction can be carried out in a liquid phase. Although the solvent is not particularly limited, aromatic hydrocarbon such as benzene, toluene, xylene or mesitylene, or a substituted aromatic compound such as dichlorobenzene is suitable, which does not react with the bifunctional silane compound [I] and is stable under the reaction temperature. Pressure in the reaction can be usually an ambient pressure, however, the reaction can be also carried out under a pressurized condition of 0.15 to 0.49 MPa. The reaction time is preferably 0.5 to 20 hrs, and more preferably 3 to 10 hrs. Amount of the bifunctional silane compound [I] is preferably 0.01 to 10, and more preferably 0.05 to 1 as represented by weight ratio of the bifunctional silane compound [I]/silica gel. It is also preferred that a basic compound such as pyridine or imidazole is added to the reaction system.

The bifunctional silane compound [I] is advantageous in that it has more reactive sites and exhibits higher reactivity than monofunctional silane compounds, while causing less side reaction than trifunctional silane compounds.

In particular, use of a silane compound in which two $R^1$s are the same, and represent an alkyl group or an aryl group having 4 to 30 carbon atoms, as the bifunctional silane compound [I] is advantageous in improving hydrophobicity and resolution ability, still further durability due to increase in density of the alkyl group or the aryl group per unit area of the silica gel, unlike the case where a bifunctional silane compound in which two $R^1$s represent different alkyl groups or aryl groups (for example, octadecylmethyldichlorosilane, n-octylmethyldichlorosilane or the like) is used.

The reaction mixture after the chemical modification reaction can be directly used in the following endcapping reaction, however, the solid matter can be taken out of the chemical modification reaction mixture, and subjected to the endcapping reaction after washing and drying.

After the chemical modification reaction, to the reaction mixture, an endcapping agent can be added to conduct the endcapping reaction. However, in some cases, unreacted bifunctional silane compound [I] is hydrolysed after completing the chemical modification reaction.

The endcapping agent represented by the general formula [II] is bifunctional cyclic silazane, and preferred examples include 1,1,3,3,5,5-hexamethylcyclotrisilazane, 1,1,3,3,5,5,7,7-octamethylcyclotetrasilazane, 1,1,3,3,5,5,7,7,9,9-decamethylcyclopentasilazane, 1,1,3,3,5,5,7,7,9,9,11,11-dodecamethylcyclohexasilazane, 1,1,3,3,5,5-hexaethylcyclotrisilazane, 1,1,3,3,5,5,7,7-octaethylcyclotetrasilazane, 1,1,3,3,5,5,7,7,9,9-decaethylcyclopentasilazane, 1,1,3,3,5,5,7,7,9,9,11,11-dodecaethylcyclohexasilazane and the like.

These can be used alone, or two or more thereof can be used as a mixture.

The endcapping agent [II] can be used in combination with a bifunctional silane compound represented by the general formula [III]. Ratio of the endcapping agent [II] and the bifunctional silane compound [III] can be preferably 0.5 or greater, and more preferably 1 or greater as represented by the weight ratio of the endcapping agent [II]/bifunctional silane compound [III]:

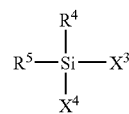

[III]

[wherein, $X^3$ and $X^4$, the same or different, represent a hydrogen atom, a halogen atom or an alkoxyl group having 1 to 4 carbon atoms; and $R^4$ and $R^5$, the same or different, represent an alkyl group having 1 to 4 carbon atoms].

Preferred Examples of the bifunctional silane compound [III] include dimethyldichlorosilane, dimethyldimethoxysilane and the like.

The present inventors performed a variety of studies, and consequently found that use of the bifunctional cyclic silazane represented by the general formula [II] in endcapping markedly improves durability of the resulting endcapping-modified silica gel than in the case where trimethylchlorosilane or hexamethyldisilazane is used as a conventional monofunctional endcapping agent.

The endcapping reaction can be carried out by a known method and under known conditions, in which the chemically modified silica gel and the endcapping agent can be heated in a solvent to permit the reaction. The reaction temperature is preferably 60 to 200° C., and more preferably 100 to 160° C. The reaction can be carried out in a liquid phase. Although the solvent is not particularly limited, aromatic hydrocarbon such as benzene, toluene, xylene or mesitylene, or a substituted aromatic compound such as dichlorobenzene is suitable, which does not react with an endcapping agent [II] and is stable under the reaction temperature. Pressure in the reaction can be preferably an ambient pressure, however, the reaction can be also carried out under a pressurized condition of 0.15 to 0.49 MPa. The reaction time is preferably 0.5 to 20 hrs, and more preferably 3 to 10 hrs. Amount of the endcapping agent [II] is preferably 0.01 to 10, and more preferably 0.05 to 1 as represented by weight ratio of the endcapping agent [II]/chemically modified silica gel. It is also preferred that a basic compound such as pyridine or imidazole is added to the reaction system.

After completing the reaction, solid-liquid separation can be carried out, and the separated solid matter can be washed sufficiently with a washing agent such as methanol, followed by drying to obtain a packing material for liquid chromatography.

ADVANTAGES OF THE INVENTION

According to the present invention, a packing material for liquid chromatography can be produced at a comparatively moderate temperature, at 200° C. or lower, thus in a simple reaction equipment and production step requiring a short time period, accordingly, at low costs.

The packing material for liquid chromatography according to the invention avoids loss of characteristics of silica gel, and exhibits high acidic resistance and alkalic resistance and has longer operating life without changing selectivity as a packing material for liquid chromatography. Therefore, this packing material is particularly suited for analysis and fractionation of a biological sample containing peptides, proteins or the like.

BEST MODE FOR CARRYING OUT THE INVENTION

Figure 1:
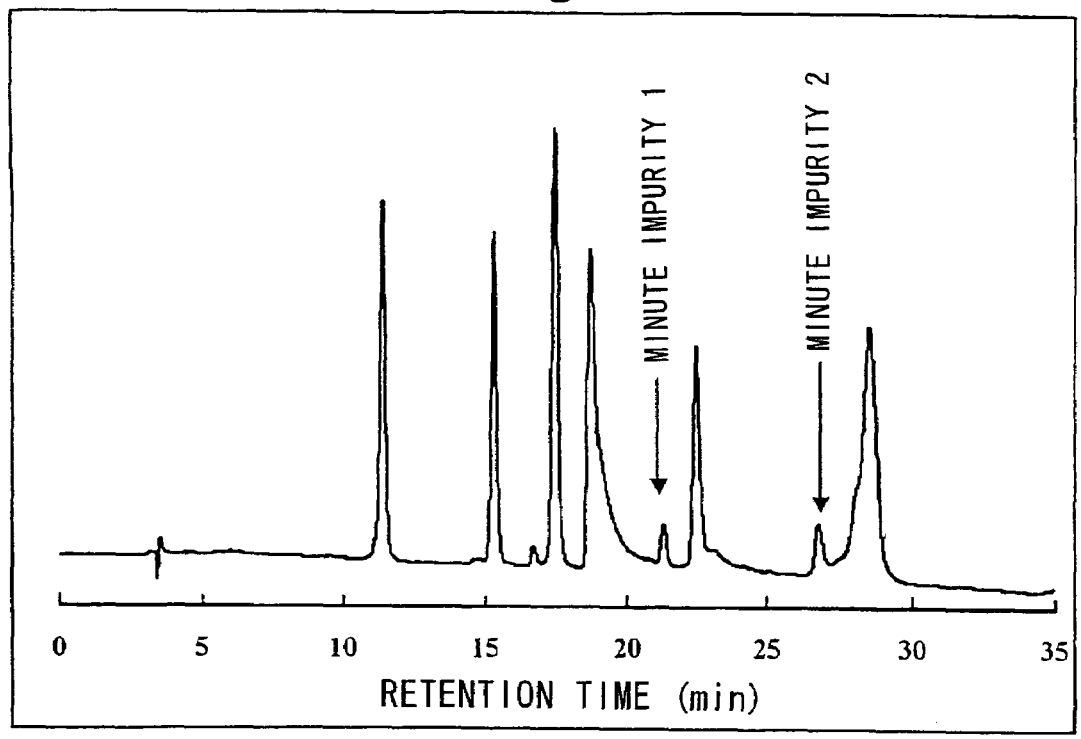
FIG. 1 illustrates a chart of liquid chromatography obtained in the seperation test of proteins using the packing material for liquid chromatography obtained in Example 1.

Hereinafter, some examples of the present invention will be demonstrated to describe the invention in detail. However, the invention is not limited by these examples. As a comparison, examples in which a conventional monofunctional silane compound and a conventional monofunctional endcapping agent were used will be illustrated. Acidic resistance comparison test, alkalic resistance comparison test, and protein separation comparison test of these examples were performed.

EXAMPLE 1

After conducting azeotropic dehydration of 20 g of spherical highly-pure silica gel (manufactured by Daiso Co., Ltd. "Daiso gel SP-300-10P", mean particle size: 10 μm, fine pore size: 300 angstrom, surface area: 100 $m^2/g$) in 150 ml of toluene, thereto were added 3.3 g of di-n-butyldichlorosilane and 2.4 g of pyridine. This mixture was heated to reflux for 5 hours. Subsequently, to this reaction mixture was added 0.8 g of 1,1,3,3,5,5-hexamethylcyclotrisilazane as an endcapping agent. This mixture was refluxed for 5 hours to complete the endcapping reaction, and was cooled to room temperature, followed by filtration, washing with methanol and drying to give 20 g of a packing material for liquid chromatography.

Comparative Example 1

After conducting azeotropic dehydration of 20 g of the same spherical highly-pure silica gel as that used in Example 1 ("Daiso gel SP-300-10P") in 150 ml of toluene, thereto were added 2.3 g of n-butyldimethylchlorosilane and 1.2 g of pyridine. This mixture was heated to reflux for 5 hours. Subsequently, to this reaction mixture were added 2.0 g of trimethylchlorosilane as an endcapping agent and 1.8 g of pyridine. This mixture was refluxed for 5 hours to complete the endcapping reaction, and was cooled to room temperature, followed by filtration, washing with methanol and drying to give 20 g of a packing material for liquid chromatography.

Comparative Example 2

After conducting azeotropic dehydration of 20 g of the same spherical highly-pure silica gel as that used in Example 1 ("Daiso gel SP-300-10P") in 150 ml of toluene, thereto were added 2.3 g of n-butyldimethylchlorosilane and 1.2 g of pyridine. This mixture was heated to reflux for 5 hours. Subsequently, to this reaction mixture was added 2.0 g of 1,1,3,3,5,5-hexamethylcyclotrisilazane as an endcapping agent. This mixture was refluxed for 5 hours to complete the endcapping reaction, and was cooled to room temperature, followed by filtration, washing with methanol and drying to give 20 g of a packing material for liquid chromatography.

Comparative Example 3

After conducting azeotropic dehydration of 20 g of the same spherical highly-pure silica gel as that used in Example 1 ("Daiso gel SP-300-10P") in 150 ml of toluene, thereto were added 3.3 g of di-n-butyldichlorosilane and 2.4 g of pyridine. This mixture was heated to reflux for 5 hours. Subsequently, to this reaction mixture were added 2.0 g of trimethylchlorosilane as an endcapping agent and 1.8 g of pyridine. This mixture was refluxed for 5 hours to complete the endcapping reaction, and was cooled to room temperature, followed by filtration, washing with methanol and drying to give 20 g of a packing material for liquid chromatography.

Evaluation Tests

1) Acidic Resistance Test

The packing materials for liquid chromatography obtained in Example 1 and Comparative Examples 1 to 3 were packed, respectively, in a stainless column having an internal diameter of 6.0 mm and a length of 250 mm by a slurry method. Retention time was measured on the acidic mobile phase before and after passing the liquid, respectively, by a liquid chromatography evaluation test using uracil and naphthalene as a standard sample, and retention coefficient (k) was determined from this measurement value.

Furthermore, in order to determine carbon content in the endcapping-modified silica gel as a packing material, measurement for an elemental analysis was performed. From these results, maintenance rate of the retention coefficient and maintenance rate of the carbon content (weight of carbon per 1 gram of the endcapping-modified silica gel) after passing the liquid of acid to those before passing the liquid of acid were calculated. These results are shown in Table 1.

By passing the liquid of the acidic mobile phase through the column, the endcapping-modified silica gel was hydrolysed by the acid to cause detachment of the modification group from the matrix silica gel. Accordingly, retention coefficient of the subject compound is declined. As is seen from Table 1, when the bifunctional silane compound [I] was used as the chemical modification agent and the bifunctional cyclic silazane [II] was used as the endcapping agent as in Example 1, the highest maintenance rate of the retention coefficient and the highest maintenance rate of the carbon content after passing the liquid of acid were exhibited. In contrast, when a conventional monofunctional silane compound was used as the chemical modification agent and/or the endcapping agent as in Comparative Examples 1 to 3, insufficient acidic resistance effect was achieved, and maintenance rate of the retention coefficient and maintenance rate of the carbon content that are lower than those in Example 1 were exhibited.

Calculation of Retention Coefficient

When retention time of uracil is represented by t1, retention time of naphthalene is represented by t2 and retention coefficient of naphthalene is represented by k, retention coefficient (k) is calculated according to the following formula:

$$k=(t2-t1)/t1$$

Conditions for Passing Liquid of the Acidic Mobile Phase

Acidic mobile phase: acetonitrile/1% aqueous trifluoroacetic acid solution (pH=1)=10/90 (volume ratio)

Flow rate: 0.9 ml/min
Temperature: 70° C.
Liquid passage time: 15 hours

Calculation of maintenance rates of retention coefficient and carbon content of naphthalene after passing the liquid of acid to those before passing the liquid of acid Maintenance rate (%)=Value after passing the liquid of acid/value before passing the liquid of acid×100.

2) Alkalic Resistance Test

The packing materials for liquid chromatography obtained in Example 1 and Comparative Examples 1 to 3 were packed, respectively, in a stainless column having an internal diameter of 6 mm and a length of 250 mm by a slurry method. Through the column was passed a liquid of an alkalic mobile phase and total amount of the eluate was recovered from the column. Then, the concentration of the eluted Si was measured by an elemental analysis of the recovered liquid. The results are shown in Table 2.

Dissolution of the matrix silica gel in the column occurs by passing the liquid of the alkalic mobile phase through the column. As is seen from Table 2, when the bifunctional silane compound [I] was used as the chemical modification agent and the bifunctional cyclic silazane [II] was used as the end-

TABLE 1

Comparison of results of acidic resistance test

|  | Example 1 | Comparative Example 1 | Comparative Example 2 | Comparative Example 3 |
| --- | --- | --- | --- | --- |
| Chemical modification agent | di-n-butyl dichlorosilane | n-butyldimethyl chlorosilane | n-butyldimethyl chlorosilane | di-n-butyl dichlorosilane |
| Endcapping agent | 1,1,3,3,5,5-hexamethyl cyclotrisilazane | trimethyl chlorosilane | 1,1,3,3,5,5-hexamethyl cyclotrisilazane | Trimethyl chlorosilane |
| Maintenance rate of retention coefficient for passage of liquid of acid (%) | 96 | 7 | 56 | 89 |
| Maintenance rate of carbon content for passage of liquid of acid (%) | 96 | 26 | 69 | 95 |

Liquid Chromatography Evaluation Test

Mobile phase: methanol/water=50/50 (volume ratio)
Flow rate: 1.7 ml/min
Temperature: 40° C.
Detector: UV 254 nm
Standard sample:
 1) uracil (0.3 mg/ml)
 2) naphthalene (1.8 mg/ml)
Injection: 1.5 µl capping agent as in Example 1, the lowest concentration of Si eluted by passage of the alkalic liquid was exhibited, in other words, the highest alkalic resistance was achieved. In contrast, when the conventional monofunctional silane compound was used as the chemical modification agent and/or the endcapping agent as in Comparative Examples 1 to 3, insufficient effect on the alkalic resistance was achieved, showing higher concentration of the eluted Si in comparison with Example 1.

TABLE 2

Comparison of results of alkalic resistance test

|  | Example 1 | Comparative Example 1 | Comparative Example 2 | Comparative Example 3 |
|---|---|---|---|---|
| Chemical modification agent | di-n-butyl dichlorosilane | n-butyldimethyl chlorosilane | n-butyldimethyl chlorosilane | di-n-butyl dichlorosilane |
| Endcapping agent | 1,1,3,3,5,5-hexamethyl cyclotrisilazane | Trimethyl chlorosilane | 1,1,3,3,5,5-hexamethyl cyclotrisilazane | Trimethyl chlorosilane |
| Concentration of Si element eluted by passing liquid of alkali (ppm) | 12 | 223 | 134 | 23 |

Conditions for Passing Liquid of Alkalic Mobile Phase
  Mobile phase: acetonitrile/0.01 N aqueous sodium hydroxide Solution (pH:12)=10/90 (volume ratio)
  Flow rate: 1.7 ml/min
  Temperature: 40° C.
  Liquid passage time: 5 hours
Measurement of Concentration of Eluted Si
  Measurement was conducted using inductively coupled plasma emission spectrometry (ICP).

3) Separation Test of Proteins

Figure 2:
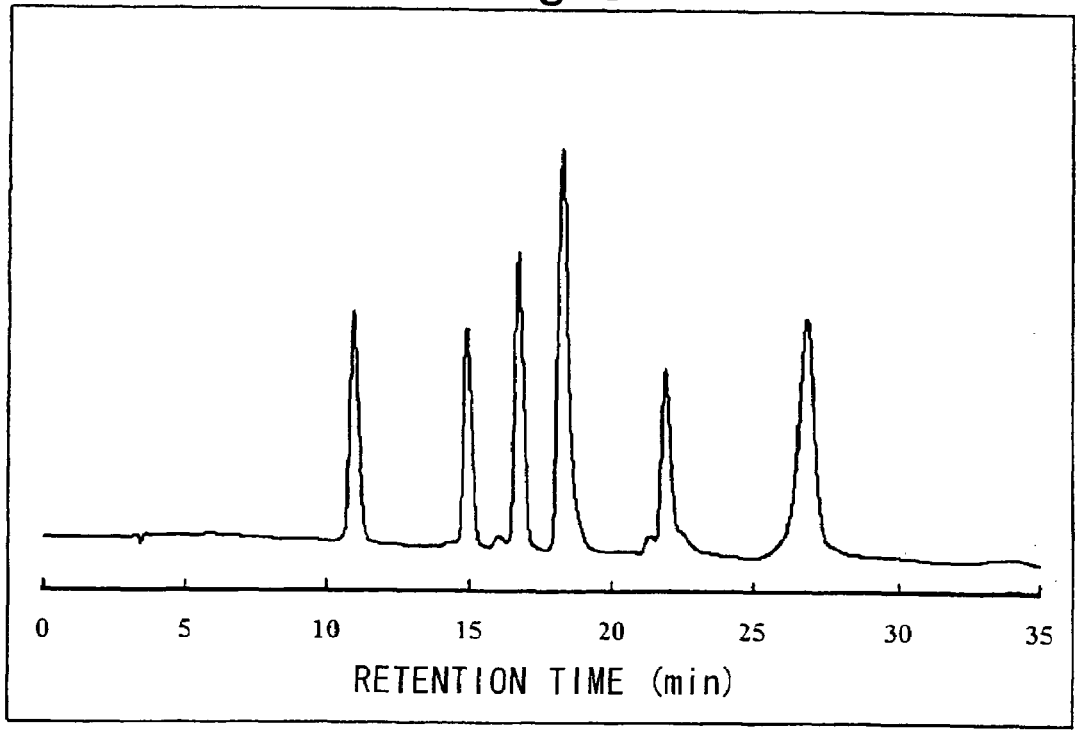
FIG. 2 illustrates a chart of liquid Chromatography obtained in the seperation test of proteins using the Packing material for liquid obtained in Comparative Example 1.

The packing materials for liquid chromatography obtained in Example 1 and Comparative Example 1 were packed, respectively, in a stainless column having an internal diameter of 6 mm and a length of 250 mm by a slurry method. Using a mixture of typical proteins as a standard sample, a liquid chromatography evaluation test was performed. Charts of liquid chromatography obtained in the separation test of proteins in which each of the packing materials of Example 1 and Comparative Example 1 was used are shown in FIG. 1 and FIG. 2, respectively.

The packing material for liquid chromatography of Example 1 prepared using the bifunctional silane compound [I] as the chemical modification agent and the bifunctional cyclic silazane [II] as the endcapping agent not only exhibited unchanged selectivity of the proteins and the order of their elution, but also enabled separation of minute impurities which could not have been separated conventionally (see, FIG. 1), thereby suggesting higher separation performance, in comparison with the packing material for liquid chromatography of Comparative. Example 1 prepared using the conventional monofunctional silane compound as the chemical modification agent and the endcapping agent.

Operation Conditions for Liquid Chromatography
  Mobile Phase
Liquid A) acetonitrile/water/trifluoroacetic acid=20/80/0.1 (volume ratio)
Liquid B) acetonitrile/water/trifluoroacetic acid=60/40/0.1 (volume ratio)
  0 to 25 min, linear gradient of from liquid A to liquid B
  25 to 35 min, liquid B 100%
  Flow rate: 1.7 ml/min
  Column temperature: 35° C.
  Detector: UV 220 nm
  Standard sample: mixture of 1) to 6)
  1) Ribonuclease A (2.0 mg/ml)
  2) Cytochrome C (1.5 mg/ml)
  3) Lysozyme (1.5 mg/ml)
  4) Bovine serum albumin (4.0 mg/ml)
  5) Myoglobin (2.0 mg/ml)
  6) Ovalbumin (5.0 mg/ml)
  Injection: 10 μl

The invention claimed is:

1. A method of the production of a packing material for liquid chromatography which comprises chemically modifying silica gel with a bifunctional silane compound represented by the general formula [I]:

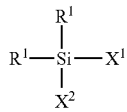

[wherein, $X^1$ and $X^2$, the same or different, represent a hydrogen atom, a halogen atom or an alkoxy group having 1 to 4 carbon atoms; and $R^1$ represents an alkyl group or an aryl group which can have substituent(s)], and carrying out an endcapping reaction of the resulting chemically modified silica gel using bifunctional cyclic silazane represented by the general formula [II]:

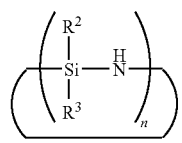

[wherein, $R^2$ and $R^3$, the same or different, represent an alkyl group having 1 to 4 carbon atoms; and n represents a value indicating unit number that forms the ring, which is an integer of 2 to 10].

2. The method of the production of a packing material for liquid chromatography according to claim 1 wherein the alkyl group represented by $R^1$ in the general formula [I] has an aryl group, an amino group, a cyano group or a nitro group at the end thereof, or has an amide group, a carbamate group, a carbamide group, an ester group or a carbonate group at a site other than the end thereof.

3. The method of the production of a packing material for liquid chromatography according to claim 1 or 2 wherein bifunctional cyclic silazane represented by the general formula [II] and a bifunctional silane compound represented by the general formula [III]:

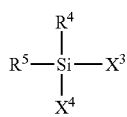

[wherein, $X^3$ and $X^4$, the same or different, represent a hydrogen atom, a halogen atom or an alkoxyl group having 1 to 4 carbon atoms; and $R^4$ and $R^5$, the same or different, represent an alkyl group having 1 to 4 carbon atoms] are used in combination.

* * * * *